(12) United States Patent
Jahns et al.

(10) Patent No.: US 9,039,947 B2
(45) Date of Patent: May 26, 2015

(54) METHODS FOR MAKING LAYERED DENTAL APPLIANCES FROM THE OUTSIDE IN

(75) Inventors: Michael Jahns, Gilching (DE); Gallus Schechner, Seefeld (DE); Martin Goetzinger, Eching am Ammersee (DE); Holger Hauptmann, Sindelsdorf (DE); Andreas Herrmann, Steinebach (DE); Marco Sartory, Peissenberg (DE)

(73) Assignee: 3M Innovative Properties Company, St. Paul, MN (US)

( * ) Notice: Subject to any disclaimer, the term of this patent is extended or adjusted under 35 U.S.C. 154(b) by 161 days.

(21) Appl. No.: 13/497,359

(22) PCT Filed: Sep. 23, 2010

(86) PCT No.: PCT/US2010/049897
§ 371 (c)(1),
(2), (4) Date: Mar. 21, 2012

(87) PCT Pub. No.: WO2011/041193
PCT Pub. Date: Apr. 7, 2011

(65) Prior Publication Data
US 2012/0175801 A1 Jul. 12, 2012

Related U.S. Application Data

(60) Provisional application No. 61/247,246, filed on Sep. 30, 2009.

(51) Int. Cl.
*A61C 13/08* (2006.01)
*B29C 43/14* (2006.01)
(Continued)

(52) U.S. Cl.
CPC .............. *A61C 13/081* (2013.01); *B29C 43/146* (2013.01); *A61C 13/09* (2013.01);
(Continued)

(58) Field of Classification Search
CPC ...................................................... A61C 13/081
See application file for complete search history.

(56) References Cited

U.S. PATENT DOCUMENTS 2,271,454 A 1/1942 Erdle
2,439,138 A 4/1948 Kohrman
(Continued)

FOREIGN PATENT DOCUMENTS

CN 101505679 8/2009
DE 747491 1/1953
(Continued)

OTHER PUBLICATIONS

K. Prabhakaran, "Casting of Alumina Using Boehmite as a Binder", Journal Eur. Ceram. Soc., 19 (1999) 2875-2881.
(Continued)

*Primary Examiner* — Benjamin Schiffman
(74) *Attorney, Agent, or Firm* — Nicole J. Einerson

(57) ABSTRACT

A system and method for making a layered dental appliance. The system can include a first portion comprising a negative of a first layer of a layered dental appliance, and a second portion comprising a positive shape of a second layer of the layered dental appliance. The method can include providing a mold comprising a negative of an outer shape of a layered dental appliance, and positioning a slurry in the mold, forming a first layer of the layered dental appliance. The method can further include providing a solid structure comprising a positive shape of a second layer of the layered dental appliance, and pressing the solid structure into the slurry in the mold.

16 Claims, 1 Drawing Sheet

(51) Int. Cl.
 *B29C 43/20* (2006.01)
 *A61C 13/09* (2006.01)
 *A61C 13/00* (2006.01)

(52) U.S. Cl.
 CPC ......... *B29C2043/148* (2013.01); *B29C 43/203* (2013.01); *A61C 13/0003* (2013.01); *B29C 2043/147* (2013.01)

(56) References Cited

U.S. PATENT DOCUMENTS

| | | | |
|---|---|---|---|
| 2,474,676 A | 6/1949 | Kelly | |
| 2,514,076 A | 7/1950 | Kelly | |
| 3,810,773 A | 5/1974 | Shannon | |
| 4,078,310 A | 3/1978 | Horger | |
| 4,115,487 A | 9/1978 | Rockett | |
| 4,321,042 A | 3/1982 | Scheicher | |
| 4,937,928 A | 7/1990 | Van der Zel | |
| 5,028,362 A | 7/1991 | Janney | |
| 5,145,908 A * | 9/1992 | Jenny et al. | 524/827 |
| 5,204,055 A | 4/1993 | Sachs | |
| 5,342,201 A | 8/1994 | Oden | |
| 5,697,043 A | 12/1997 | Baskaran | |
| 5,989,031 A | 11/1999 | Kura | |
| 6,395,202 B1 | 5/2002 | Nagel | |
| 6,648,645 B1 | 11/2003 | MacDougald | |
| 6,869,552 B2 | 3/2005 | Glidewell | |
| 6,955,776 B1 | 10/2005 | Feenstra | |
| 7,086,863 B2 | 8/2006 | Van der Zel | |
| 7,181,862 B2 | 2/2007 | Boara | |
| 7,236,842 B2 | 6/2007 | Kopelman | |
| 7,384,470 B2 | 6/2008 | Binkle | |
| 7,446,057 B2 | 11/2008 | Bietsch | |
| 7,536,234 B2 | 5/2009 | Kopelman | |
| 7,689,310 B2 | 3/2010 | Kopelman | |
| 2002/0157419 A1 | 10/2002 | Ganguli | |
| 2003/0222366 A1 | 12/2003 | Stangel | |
| 2005/0023710 A1 | 2/2005 | Brodkin | |
| 2006/0008777 A1 | 1/2006 | Peterson | |
| 2006/0151911 A1 * | 7/2006 | Zollner et al. | 264/255 |
| 2006/0257824 A1 | 11/2006 | Pfeiffer | |
| 2007/0092853 A1 | 4/2007 | Liu | |
| 2008/0131841 A1 | 6/2008 | Taub | |
| 2008/0206460 A1 | 8/2008 | Rhoades | |
| 2008/0241788 A1 | 10/2008 | Bauer | |
| 2008/0302135 A1 | 12/2008 | Costa | |
| 2008/0318189 A1 | 12/2008 | Brodkin | |
| 2009/0215010 A1 | 8/2009 | Tagami | |
| 2009/0233258 A1 | 9/2009 | Luthardt | |
| 2009/0274993 A1 * | 11/2009 | Bergstrom et al. | 433/201.1 |
| 2009/0311649 A1 | 12/2009 | Detje | |
| 2009/0311650 A1 | 12/2009 | Stephan | |
| 2010/0167238 A1 | 7/2010 | Kopelman | |
| 2010/0233655 A1 | 9/2010 | Karim | |
| 2010/0248189 A1 | 9/2010 | Burger | |

FOREIGN PATENT DOCUMENTS

| | | |
|---|---|---|
| DE | 19922870 | 7/2000 |
| EP | 0311214 | 4/1989 |
| EP | 0455854 | 11/1991 |
| EP | 0943296 | 9/1999 |
| EP | 1250895 | 10/2002 |
| EP | 1258456 | 11/2002 |
| EP | 1252867 | 7/2005 |
| EP | 1561433 | 8/2005 |
| EP | 1661866 | 5/2006 |
| EP | 1972321 | 9/2008 |
| EP | 1992302 | 11/2008 |
| FR | 998598 | 1/1952 |
| GB | 418160 | 10/1934 |
| GB | 566 518 | 1/1945 |
| JP | 01-258920 | 10/1989 |
| JP | 0282966 | 3/1990 |
| JP | 2004180976 | 7/2004 |
| JP | 2004-298599 | 10/2004 |
| WO | WO 94/27517 | 12/1994 |
| WO | WO 97/44291 | 11/1997 |
| WO | WO 01/13814 | 3/2001 |
| WO | WO 01/53225 | 7/2001 |
| WO | WO 03/093195 | 11/2003 |
| WO | WO 2004/063105 | 7/2004 |
| WO | WO 2006/120255 | 11/2006 |
| WO | WO 2007/028787 | 3/2007 |
| WO | WO 2007/051447 | 5/2007 |
| WO | WO 2009/070469 | 6/2009 |
| WO | WO 2010/039910 | 4/2010 |
| WO | WO 2010/053698 | 5/2010 |
| WO | WO 2010/074890 | 7/2010 |
| WO | WO 2010/110650 | 9/2010 |
| WO | WO 2010/110662 | 9/2010 |
| WO | WO 2011/041182 | 4/2011 |
| WO | WO 2011/041194 | 4/2011 |
| WO | WO 2011/075349 | 6/2011 |

OTHER PUBLICATIONS

Ullmann's Encyclopedia of Industrial Chemistry (2008), Chapter Silica, Section 4.1 and 5.2.
Ullmann's Encyclopedia of Industrial Chemistry (2005) Chapter Inorganic Polymers, pp. 1-39.
Beuer et al., "High-Strength CAD/CAM-fabricated veneering material sintered to zirconia coping s—A new fabrication mode for all-ceramic restorations"; Dental Materials 25 (2009) 121-128.
International Search Report PCT/US2010/049897, Jan. 14, 2011, 3 pages.
Chinese Search Report dated Apr. 23, 2014 for Chinese Patent Application No. 201080043187.3.

* cited by examiner

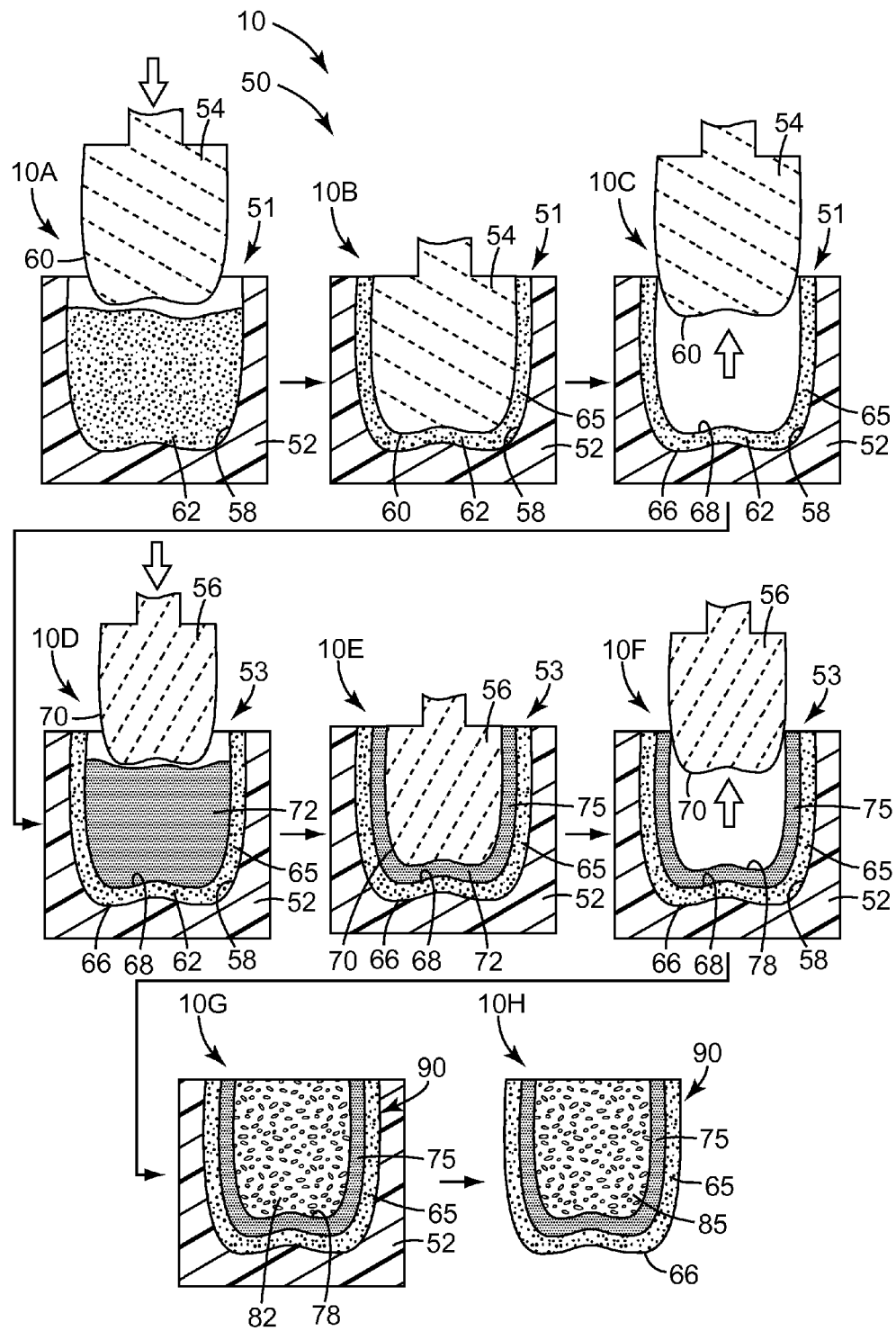

METHODS FOR MAKING LAYERED DENTAL APPLIANCES FROM THE OUTSIDE IN

CROSS REFERENCE TO RELATED APPLICATIONS

This is a national stage filing under 35 U.S.C. 371 of PCT/US2010/049897, filed 23 Sep. 2010, which claims priority to U.S. Provisional Application No. 61/247,246, filed 30 Sep. 2009, the disclosure of which is incorporated herein by reference in its entirety.

FIELD

The present disclosure is generally directed to systems and methods for making dental appliances, and particularly, to systems and methods for making layered dental appliances.

BACKGROUND

Some existing dental restorations, such as crowns, formed of glass or glass ceramic materials are produced by grinding bodies of compacted and heat treated glass or glass ceramic particles. Such bodies can be produced by mechanical compacting (e.g. uniaxial pressing) of inorganic powders often together with an organic binder first. The shape of the resulting compacted body can be limited to the shape of the compacting tool used. In some cases, cylindrical or cuboid shaped bodies can be obtained. Such compacted bodies can then undergo a heat treatment to increase the mechanical strength of the compacted bodies. Such a heat treatment can take place at a temperature that causes at least partial sintering of the powder. During such a sintering step, the density of the body of compacted powder can be increased. The resulting compacted and heat treated bodies can then be adhesively fixed in a frame or attached to a holder to prepare them for grinding to a desired shape (e.g. a dental crown or dental facing). The ground bodies can then be removed from the frame. Machining of the compacted bodies which have not been heat treated may not be possible due to the low mechanical strength of the compacted powder.

In addition, in some existing dental systems, a core is milled and then sintered (e.g., to full density). A veneer can also be milled from a mill blank and fused to the core, for example, with a slurry forming an intermediate layer between the core and the veneer. The veneer can then be sintered to the core.

Moreover, in some existing dental systems, dental restorations, such as crowns, can be produced using a manual process of covering a core layer-by-layer with veneering slurries (e.g., using a small brush). Firing steps can be included after application of each layer.

SUMMARY

Some aspects of the present disclosure provide a method for making a layered dental appliance. The method can include providing a mold comprising a negative of an outer shape of a layered dental appliance. The method can further include positioning a slurry in the mold, forming a first layer of the layered dental appliance. The method can further include providing a solid structure comprising a positive shape of a second layer of the layered dental appliance, and pressing the solid structure into the slurry in the mold.

Some aspects of the present disclosure provide a method for making a layered dental appliance. The method can include providing a mold comprising a negative of a first layer of a layered dental appliance. The method can further include providing a stamp comprising a positive shape of a second layer of the layered dental appliance. The method can further include positioning a first slurry in the mold, and pressing the stamp into the first slurry in the mold to form a cavity comprising a negative of the second layer in the first slurry. The method can further include removing the stamp from the first slurry, and positioning a material in the cavity to form another layer of the layered dental appliance, wherein the material comprises at least one of a dental core and a second slurry.

Some aspects of the present disclosure provide a method for making a layered dental appliance having n layers. The method can include providing a mold comprising a negative of a layer n−1 of a layered dental appliance. The method can further include positioning a slurry in the mold to form layer n−1 of the layered dental appliance. The method can further include pressing a dental core in the slurry, such that the dental core forms at least a portion of a layer n of the layered dental appliance.

Some aspects of the present disclosure provide a system for making a layered dental appliance. The system can include a first portion comprising a negative of a first layer of a layered dental appliance, and a second portion comprising a positive shape of a second layer of the layered dental appliance. The system can further include a first slurry configured to be positioned between the first portion and the second portion, such that the first slurry forms the first layer of the layered dental appliance.

Some aspects of the present disclosure provide a system for making a layered dental appliance. The system can include a first portion comprising a negative of a first layer of a layered dental appliance, and a second portion comprising a positive shape of a second layer of the layered dental appliance. The system can further include a third portion comprising a positive shape of a third layer of the layered dental appliance.

Other features and aspects of the present disclosure will become apparent by consideration of the detailed description and accompanying drawings.

BRIEF DESCRIPTION OF THE DRAWINGS

FIG. 1 is a schematic flowchart of a method according to one embodiment of the present disclosure and illustrates a system according to one embodiment of the present disclosure.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the term "coupled" and variations thereof is used broadly and encompasses both direct and indirect couplings. Further, "coupled" is not restricted to physical or mechanical connections or couplings. It is to be understood that other embodiments may be utilized, and structural or logical changes may be made without departing from the scope of the present disclosure.

The present disclosure generally relates to systems and methods for making layered dental appliances, such as dental restorations. In some embodiments, a dental appliance such as a dental restoration, can be desired that not only meets the performance or material requirements but is also visually indistinguishable from adjacent natural tooth surfaces. A layered dental appliance can have improved aesthetics over a single layer or single material appliance, for example, if one or more layers toward the outer surface of the appliance are more translucent than inner layer(s), such that the appliance (e.g., restoration) more closely mimics the appearance of a natural tooth.

In some embodiments, the systems and methods of the present disclosure may not be performed in situ, or in a patient's mouth. Rather, in some embodiments, the systems and methods of the present disclosure can be employed in a laboratory setting, such as in a dental laboratory. That is, in some embodiments, the methods of the present disclosure can be referred to as lab-bench, desktop, or laboratory procedures.

Some systems and methods of the present disclosure can produce net-shape or near-net-shape dental appliances (e.g., restorations) via a gel casting process (e.g., a sol-gel casting process), for example, using silica glass as an inorganic binder. Multiple casting steps can be performed consecutively to achieve layered structures.

Some systems and methods of the present disclosure can include providing a multi-part (e.g., two-part) mold that includes both a negative of an outer shape of a layer (e.g., a negative of the desired outer shape of the resulting restoration) and a positive of an inner shape of the layer. In such systems and methods, a layered dental appliance can be formed using a gel casting process that can include providing a mold comprising a negative of an outer shape of a layered dental appliance; positioning a slurry in the mold; forming a first layer of the layered dental appliance; providing a solid structure comprising a positive shape of a second layer of the layered dental appliance; and pressing the solid structure into the slurry in the mold. In some embodiments, the mold and the solid structure can form a two-part mold.

In some embodiments, the mold can actually include more than two parts, because a variety of "positive" molds (or positive portions of the molds) can be provided to form successively inner layers. For example, a first positive mold can be used with the negative mold to form a first (outer) layer of a dental appliance, and a second positive mold can be used (e.g., with the same negative mold plus the first layer) to form a second layer that is an inner layer with respect to the first layer, and so on. Following the methods of the present disclosure, the outermost layer of the dental appliance would be formed first, followed by the next inner layer, followed by the next inner layer, etc. As a result, the methods of the present disclosure can sometimes be referred to as an "outside-in" method of making a layered dental appliance.

The term "dental article" is to be understood as an article which can and is to be used in the dental or orthodontic area including dental laboratories.

The term "dental appliance" generally refers to any dental or orthodontic restoration, dental mill blank, prosthetic device, or combination thereof. The appliance may be a finished appliance ready for introduction into the mouth of a patient, an appliance without the finishing (e.g. without stains) but with its final shape (i.e., a "net shape" appliance), or it may be a preformed or near-final dental appliance (i.e., a "near-net shape" appliance) subject to further processing before use, such as a dental mill blank.

The phrase "dental mill blank" generally refers to a solid block of material from which a desired product (e.g., a dental restoration) can be machined. A dental mill blank may have a size of about 10 mm to about 30 mm in two dimensions, for example may have a diameter in that range, and may be of a certain length in a third dimension. A blank for making a single crown may have a length of about 15 mm to about 30 mm, and a blank for making bridges may have a length of about 40 mm to about 80 mm. In some embodiments, a blank used for making a single crown can have a diameter of about 24 mm and a length of about 19 mm. In some embodiments, a blank used for making bridges can have a diameter of about 24 mm and a length of about 58 mm.

The term "machining" generally refers to shaping a material by a machine, and can include, but is not limited to one or more of milling, grinding, cutting, carving, or a combination thereof. In some cases, milling can be faster and more cost-effective than grinding.

The phrase "dental workpiece" generally refers to a dental appliance which has been further processed (e.g. by machining) to obtain an intentionally shaped product. A dental workpiece can be further processed (e.g. by sintering) or used as such.

The phrase "dental restoration" is generally used to refer to any restoration that can be used in the dental field, including, but not limited to, crowns, partial crowns, inlays, onlays, abutments, bridges (e.g., including 2-part, 3-part, 4-part, 5-part or 6-part bridges), implants, other suitable dental articles, and combinations thereof. The dental restoration can include a three-dimensional inner and outer surface including convex and concave structures. Compared to other ceramic articles, such as pottery or paving stones, dental restorations can be relatively small and can include filigree. The thickness of a dental restoration can vary from very thin, for example at its edges and rims (e.g., less than about 0.1 mm) to considerably thick, for example, in the biting, or occlusal, area (e.g., up to about 7 mm). In some embodiments, the thickness of a dental restoration ranges from 0.3 mm to 0.5 mm. In some embodiments, the dental restoration can comprise or consist essentially of a glass; glass ceramic; polycrystalline ceramic material, for example, comprising alumina (e.g., $Al_2O_3$), zirconia ($ZrO_2$), partly or fully stabilized zirconia (e.g., Yttrium-stabilized zirconia), titanium dioxide ($TiO_2$), high-strength oxides of the elements of the main groups II, III and IV and the subgroups III and IV, and their mixtures; metals, metal alloys, precious metals, precious metal alloys, or combinations thereof (e.g., cobalt alloys, such as cobalt-chromium, titanium alloys, gold/platinum/palladium alloys, etc., and combinations thereof); and combinations thereof. In some embodiments, the dental restoration can include at least two layers, for example, a dental core (or dental framework) and a dental veneer.

The phrase "dental core" or "dental framework" generally refers to a solid structure that can be pre-fabricated or at least partially pre-fabricated and then used as the innermost core or center layer of the layered dental appliance of the present disclosure. For example, in some embodiments, the dental core can be adapted to be coupled to or to fit over one or more of a tooth stump, an implant abutment, or the like, or combinations thereof.

The phrase "dental veneer" generally refers to a structure formed of one or more layers that can be coupled (e.g., fused) to or built upon another structure (e.g., a dental core) for color, aesthetics, texture, surface properties, etc., and, in some embodiments, to mimic the appearance of a natural tooth.

A dental core (sometimes referred to as a "dental framework") and a dental veneer can each include a three-dimensional inner and outer surface including convex and concave structures. The outer surface of the dental core can correspond to an inner surface of the dental veneer. The inner surface of the dental core can correspond to an outer surface of a prepared tooth stump, whereas the outer surface of the dental veneer can correspond to the desired (e.g., final) dental restoration.

Dental cores or frameworks can be made of or comprise at least one of a ceramic, a metal, a metal alloy, a precious metal, a precious metal alloy, and combinations thereof. Examples of ceramics can include, but are not limited to, alumina (e.g., $Al_2O_3$); zirconia ($ZrO_2$); partly or fully stabilized zirconia (e.g., Yttrium-stabilized zirconia); titanium dioxide ($TiO_2$); high-strength oxides of the elements of the main groups II, III and IV and the subgroups III and IV, and combinations thereof and combinations thereof. Examples of metals, metal alloys, precious metals, and precious metal alloys can include, but are not limited to, cobalt alloys (e.g., cobalt-chromium), titanium alloys, gold/platinum/palladium alloys, and combinations thereof.

Compared to other framework such as pottery or paving stones, dental cores or framework can be small and filigree, and of high strength. The thickness of the dental framework can vary from very thin, e.g. at the edges and rims (below about 0.1 mm) to considerably thick, e.g. in the biting area (up to about 7 mm).

Dental veneers can include one or more layers that would be coupled (e.g., fused) to or built upon an inner core or center of a dental appliance. Dental veneers can also be small and filigree objects. The strength of dental veneers, however, can be less compared to dental frameworks. Dental veneers can be made of or comprise glass and/or glass ceramic materials. Examples of suitable glass materials include, but are not limited to, silica ($SiO_2$) in combination with one or more of alumina ($Al_2O_3$), potassium oxide ($K_2O$), sodium oxide ($Na_2O$), etc., and combinations thereof. Examples of suitable glass ceramic materials include, but are not limited to a material having a glass fraction comprising silica ($SiO_2$) in combination with one or more of alumina ($Al_2O_3$), potassium oxide ($K_2O$), sodium oxide ($Na_2O$), etc., and combinations thereof, and a crystalline fraction comprising e.g. leucite, lithium disilicate, etc., and combinations thereof.

In some embodiments, it can be important to match the coefficient of thermal expansion (CTE) of the dental core with that of a dental veneer (or a portion of the dental veneer). Otherwise, in some cases, the veneer and the core may not be fused correctly during firing which might lead to failure of the restoration. In some embodiments, glass itself (e.g., including some of the formulations listed above) may match that of zirconia.

In some embodiments, for example, when a dental core comprises alumina and/or metal, which tend to have a higher CTE, a crystalline material (e.g., leucite) may need to be added to the glass forming the veneer. Adding leucite to glass can raise the CTE of the glass, and can also improve the mechanical strength of the glass, but crystal materials other than leucite can also be used. The amount of leucite (or other crystal phase) to be added to the glass can depend on the material makeup of the dental core to which the dental veneer will be coupled (e.g., fused), because different metals and alloys have different CTEs. Table 1 lists exemplary pairings of dental core and dental veneer materials. Table 1 is only intended to be illustrative and not limiting:

TABLE 1

Exemplary pairings of dental core and dental veneer materials

| Dental Core materials | Dental Veneer materials |
|---|---|
| Zirconia | glass (e.g., SiO2 with Al2O3, K2O, Na2O, etc.) |
| Alumina | glass ceramic: glass fraction (e.g., SiO2 with Al2O3, K2O, Na2O, etc.) and crystalline fraction (e.g. leucite) |
| Metal | glass ceramic: glass fraction (e.g., SiO2 with Al2O3, K2O, Na2O, etc.) and crystalline fraction (e.g. leucite) |

The term "glass" generally refers to a hard, brittle, transparent solid. Examples of glasses can include, but are not limited to, soda-lime glass and borosilicate glass. A glass can include an inorganic product of fusion that has been cooled to a rigid condition without crystallizing. Some glasses contain silica as their main component and a certain amount of glass former.

The phrase "glass ceramic" generally refers to a material sharing many properties with both glass and more traditional crystalline ceramics. It is formed as a glass, and then made to crystallize partly by heat treatment. Unlike sintered ceramics, glass-ceramics have no pores between crystals. Instead, the space between the crystallites is filled by the glassy matrix. Glass ceramics mainly refer to a mixture of alkali metal-, silicon-, and aluminium-oxides.

The term "ceramic" generally refers to an inorganic non-metallic material that can be produced by application of heat. Ceramics can be hard, porous and brittle and, in contrast to glasses or glass ceramics, can display an essentially purely crystalline structure.

A dental ceramic appliance can be classified as "pre-sintered" within the meaning of the present disclosure if the dental ceramic appliance has been treated with heat (e.g., a temperature ranging from about 900 to about 1100° C.) for about 1 to about 3 hours to such an extent that the raw breaking resistance (Weibull strength Sigma 0) of the dental ceramic appliance is within a range of about 15 to about 55 MPa or about 30 to about 50 MPa (measured according to the "punch on three ball test" (biaxial flexural strength) described in DIN EN ISO 6872, edition March 1999, with the following modifications: diameter of steel ball: 6 mm; diameter of support circle: 14 mm; diameter of flat punch: 3.6 mm; diameter of sample disc: 25 mm, thickness of sample disc: 2 mm; no grinding and polishing of samples).

A pre-sintered dental ceramic appliance can include a porous structure and its density (e.g., which can be 3.0 g/cm$^3$ for an Yttrium stabilized $ZrO_2$ ceramic) can be less compared to a completely sintered or finally sintered (or "finely sintered"; i.e., such that there will be no further sintering step) dental ceramic appliance (e.g., which can be 6.1 g/cm$^3$ for an Yttrium stabilized $ZrO_2$ ceramic). In some embodiments, the diameter of the pores can be in a range of about 50 nm to about 150 nm (corresponding to about 500 to about 1500 Å). In some embodiments, a pore diameter can be about 120 nm.

In some embodiments, pre-sintering of a glass and/or glass ceramic material can be effected in a temperature range of about 500 to about 750° C.

The term "sintering" generally refers to making objects from a powder by heating the material (e.g., below its melting point—"solid state sintering") until its particles adhere to each other. Sintering can cause the densification of a porous material to a less porous material (or a material having less cells) having a higher density. In some cases, sintering can also include changes of the material phase composition (e.g., a partial conversion of an amorphous phase toward a crystalline phase).

The terms "sintering" and "firing" are used interchangeably herein. A pre-sintered ceramic framework can shrink during a sintering step, that is, if an adequate temperature is applied. The sintering temperature to be applied depends on the ceramic material chosen. For example, for $ZrO_2$-based ceramics, a sintering temperature can range from about 1200° C. to about 1500° C. In some embodiments, $Al_2O_3$-based ceramics can be sintered at a temperature ranging from about 1300° C. to about 1700° C. In some embodiments, glass ceramic materials can be sintered at a temperature ranging from about 700 to about 1100° C. for about 1 to about 3 hours. In some embodiments, a firing step of the present disclosure can include firing at a temperature of at least about 500° C., in some embodiments, at least about 700° C., in some embodiments, at least about 1000° C., and in some embodiments, at least about 1200° C.

The unit "cells per $mm^2$" is related to the number of cells present on a cross section of the sample to be analysed. A suitable test method is given in DIN 13925.

The term "casting" generally refers to a manufacturing process by which a liquid material (e.g. solution or dispersion) is poured into a mold, which contains a hollow cavity (i.e., negative) of the desired shape, and then allowed to solidify.

A "sol-gel reaction" is a wet-chemical technique (sometimes also referred to as "Chemical Solution Deposition") for the fabrication of materials starting either from a chemical solution or colloidal particles (e.g. nanoscale particle) to produce an integrated network (gel). In some embodiments, sol-gel precursors can include metal alkoxides and metal chlorides, which undergo hydrolysis and polycondensation reactions to form a colloid, a system composed of solid particles (e.g., with sizes ranging from 1 nm to 1 μm) dispersed in a solvent. The sol can then evolve toward the formation of an inorganic continuous network containing a liquid phase (gel). Formation of a metal oxide can include connecting the metal centers with oxo (M-O-M) or hydroxo (M-OH-M) bridges, therefore generating metal-oxo or metal-hydroxo polymers in solution. A drying process can serve to remove the liquid phase from the gel thus forming a porous material. Afterwards, a thermal treatment (e.g., firing) may be performed in order to favor further polycondensation and enhance mechanical properties.

The phrase "porous material" can generally refer to a material comprising a partial volume that is formed by voids, pores, or cells in the technical field of ceramics.

A "liquid" is any solvent or liquid which is able to at least partially disperse or dissolve an inorganic binder of a slurry or mixture composition at ambient conditions (e.g., 23° C., 1013 mbar).

A composition or solution is "essentially or substantially free of" a certain component within the meaning of the present disclosure if the composition or solution does not contain said component as an essential feature. That is, such a component is not willfully added to the composition or solution either as such or in combination with other components or as an ingredient of other components. In some embodiments, a composition being essentially free of a certain component usually contains the component in an amount of less than about 1 wt.-%, in some embodiments less than about 0.1 wt.-%, in some embodiments less than about 0.01 wt.-%, and in some embodiments less than about 0.001 wt.-%, with respect to the whole composition. In some embodiments, "essentially or substantially free of" generally refers to the composition or solution not containing the component at all. However, sometimes the presence of a small amount of the component may not be avoidable, e.g. due to impurities being present in the raw materials used.

As mentioned above, some systems and methods of the present disclosure provide individually shaped, layered dental appliances with complex shapes relatively quickly using a gel casting process. In some embodiments, a sol-gel casting process is employed in which a slurry or mixture is formed by combining:

(i) a glass and/or glass ceramic powder;
(ii) a liquid (e.g., water);
(iii) a binder (e.g., an inorganic binder); and
(iv) an activator (e.g., an acid or base).

In some embodiments, the slurry comprises components (i), (ii) and (iii), and the activator (component (iv)) is not added until just prior to casting.

By providing a mixture comprising a liquid, a binder (e.g., an inorganic binder), and glass and/or glass ceramic powder or particles, a sol-gel process can be initiated resulting in a homogeneous distribution of the glass and/or glass ceramic powder or particles in an inorganic network. In contrast to this, blocks produced by uniaxial pressing sometimes are inhomogeneous with regard to density. This may be caused by an inhomogeneous pressure distribution in the pressing matrix.

Compared to a dental appliance manufactured by a pressing process and having insufficient strength unless it is pre-sintered, the dental appliance obtainable according to the gel casting process of the present disclosure has sufficient strength and can be machined without pre-sintering the dental appliance beforehand.

Moreover, machining is not limited to grinding only but can also be accomplished by milling as well. As outlined above, the strength of the dental appliance is high enough that the dental appliance can be machined without a sintering step, but low enough that the dental appliance can be shaped by applying the more efficient (e.g. faster and cheaper) milling process.

Furthermore, by using an inorganic binder for creating an inorganic network instead of an organic binder, there are less exhaust gases evaporating from the dental appliance during a later heating or sintering step. Organic binders typically produce gases like carbon and/or nitrogen oxides. Examples of inorganic binders according to the present disclosure, if at all, only produce low boiling solvents like alcohols (e.g. methanol and ethanol) which typically evaporate during the drying step.

In addition and in contrast to pressing techniques which can be limited to specific shapes (e.g., cube and cylinder), the casting process of the present disclosure facilitates the manufacturing of complex shapes. The shape of the obtained dental appliance is only limited to the shape of the mold used. Thus, objects with convex and/or concave structures can be manufactured.

Compared to pre-sintered dental appliances, the dental appliances obtained by the process of the present disclosure can have a lower density. The lower density can facilitate machining of the dental appliance (e.g. extended service life of machining tools), and can also reduce the amount of waste that is produced during the shaping process.

Some methods of the present disclosure facilitate providing colored dental appliances. Coloring additives can be added very early in the process (e.g. when the mixture to be casted is provided) and/or later on in the process (e.g. after the drying step). If the coloring is to be done after the drying step, it can be done by using a coloring solution containing coloring additives (e.g. metal salts).

Adding coloring additives at an early stage in the process, for example when providing the mixture to be casted, can result in a homogenous distribution of the coloring additives throughout the resulting dental appliance, or throughout a layer of the resulting layered dental appliance.

The amount of inorganic binder precursor used can allow for adjusting or influencing the gel time and block toughness. The amount of powder and water used can also allow for adjusting the density of the dried blocks.

FIG. 1 illustrates a schematic flowchart of a method 10 according to one embodiment of the present disclosure and a system 50 according to one embodiment of the present disclosure. The illustrated method 10 includes steps 10A-10H, and the system 50 includes a mold 52, a first solid structure 54, and a second solid structure 56, and can further include one or more slurries, as described in greater detail below. In some embodiments, as shown in FIG. 1, the system 50 includes a first mold assembly 51 that comprises the base mold (or "negative" mold) 52 and the first solid structure (or first "positive" mold) 54, and a second mold assembly 53 that comprises the base mold (or "negative" mold) 52 and the second solid structure (or second "positive" mold) 56.

In some embodiments, the mold assemblies 51 and 53 can each or collectively be referred to simply as a mold or system comprising a first portion 52 (e.g., a negative portion comprising a cavity), a second portion 54 (e.g., a first positive portion, such as a stamp, comprising a protrusion), and/or a third portion 56 (e.g., a second positive portion, such as a stamp, comprising a protrusion). In embodiments of the method 10 and system 50 that are adapted for creating more than three layers, the mold or system can include more than three portions, respectively.

In some embodiments, the system 50 itself can be described as a mold system or assembly that includes a first portion 52 comprising a negative of an outer shape (e.g., of a first layer) of the desired dental appliance, and a second portion 54 comprising a positive shape of a second layer. In some embodiments, the system 50 can further include a third portion 56 comprising a positive shape of a third layer. In some embodiments, the system can further include a fourth portion (not shown) comprising a positive shape of a fourth layer, and so on.

In the exemplary method 10 illustrated in FIG. 1, steps 10A-10C are used to form a first layer 65 of a three-layer dental appliance, and steps 10D-10F are used to form a second layer 75 of the dental appliance. In the exemplary method 10, steps 10D-10F are substantially similar to steps 10A-10C, and steps 10A-10C represent one iteration of forming a layer in the method 10, while steps 10D-10F represent another iteration of forming a layer in the method 10. That is, in the method 10 illustrated in FIG. 1, the first iteration (i.e., steps 10A-10C) is used to form a first outermost layer of the layered dental appliance, and the second iteration (i.e., steps 10D-10F) is used to form a second layer 75 that is positioned inwardly with respect to the first layer 65. As a result of the iterative nature of the method 10 shown in FIG. 1, it should be understood that any description of the elements, features and steps described with respect to steps 10A-10C (and alternatives to such elements, features and steps) also generally apply to steps 10D-10F, and vice versa. It should also be understood that the iterative steps can be repeated to achieve a layered dental appliance having as many layers as desired.

In a first step 10A of the method 10, the first mold assembly 51 is provided. The mold 52 can be adapted to receive one or more slurries and one or more solid structures 54, 56, and can include a negative shape or surface (or cavity) 58 of the outer shape (or outer layer) of the desired dental appliance.

In some embodiments, the mold 52 or mold assembly 51, 53 (e.g., one or more parts of a multi-part mold) that is used for receiving the mixture can be characterized by at least one of the following features:
- volume of the mold: can be less than about 1 $cm^3$ or can be above about 20 $cm^3$; useful ranges include 0.2 $cm^3$ to about 50 $cm^3$, or about 0.5 $cm^3$ to about 30 $cm^3$;
- dimensions of the mold: arbitrary, as long as there are no cavities too small to be filled by the reaction mixture;
- shape of the mold: arbitrary, as long as there are no cavities too small to be filled by the reaction mixture; and/or
- examples of materials of the mold (e.g., for the negative portion 52 or the positive portions 54 and 56): silicone, polyethylene (PE), polypropylene (PP), polycarbonate, polyurethane, polystyrene, polyoxymethylene, other suitable polymers, metal (e.g. steel), etc., or combinations thereof.

In some embodiments, the mold 52 or mold assembly 51, 53 (e.g., one or more parts of a multi-part mold) can have a regular (e.g., cubic, cylindrical, etc.) or irregular shape (e.g., shape of a tooth, veneer, inlay, onlay, crown, bridge, orthodontic bracket, other suitable dental appliance shapes, etc., or combinations thereof). For example, a "simple, tooth-like" shape can be used for near-net shape applications. In some embodiments, a mold having a specially designed tooth-shape can be used for net-shape applications. By way of example, in some embodiments, a specially designed tooth-shape (e.g., a positive of the tooth-shape and/or a negative of the tooth-shape) can be produced by a digital workflow, and a negative can be used as the mold or a positive can be used to form the mold. Such a digital workflow can include scanning a patient's mouth to develop a model for the desired dental appliance. Such scanning can be performed using an optical scanner that is coupled to a computer-aided design (CAD) system that functions in conjunction with a computer-integrated manufacturing (CIM) system. Such a CIM system is available, for example, under the trade designation LAVA™ from 3M ESPE AG (Seefeld, Germany).

In some embodiments, at least a portion of a mold assembly 51, 53 such as the mold 52 can be enlarged relative to the desired resulting dental appliance, for example, to accommodate for any shrinkage that may occur (e.g., when the dental appliance is fired). For example, in some embodiments, at least a portion of the mold assembly 51, 53, such as the mold 52 can be at least 110% of the size of the resulting appliance, in some embodiments, at least 150%, and in some embodiments, at least 200%.

In some embodiments, the enlargement of the mold (e.g., at least a portion of the mold assembly 51, 53, such as the mold 52) can be accomplished via computer assisted design and manufacturing (CAD/CAM), for example, by milling or printing a wax model, embedding it in a mold material and burning the wax after casting. Alternatively, in some embodiments, the mold can be milled, wax- or 3D-printed, formed by rapid prototyping, formed by stereolithography, or a combination thereof. In addition, in some embodiments, the enlargement can be accomplished via copy milling or other hand driven enlargements, e.g., by coating a hand-made wax-up with a layer of a certain thickness that corresponds to the desired percent enlargement.

In some embodiments, the mold (e.g., at least a portion of the mold assembly 51, 53) can include a holder (e.g., a holder can be embedded into the mold). That is, in some embodiments, the dental appliance after having been removed from the mold 52 can contain a holder or can be fixed to a holder. This can facilitate handling of the dental appliance in a further processing or machining step. In some embodiments, the holder can be formed of metal.

As shown in FIG. 1, in the first step 10A of the method 10, a first slurry 62 can be positioned (e.g., cast) in the mold 52. In addition, the first solid structure 54 can begin being moved toward or into the interior of the mold 52. The first solid structure 54 can include a positive shape or surface 60 corresponding to a first layer of the desired layered dental appliance. By way of example only, the first solid structure 54 (and the second solid structure 56) is shown in FIG. 1 as fitting concentrically/axially and symmetrically in the mold 52; however, it should be understood that the solid structures 54 and 56 can instead be positioned "off-center" with respect to the mold 52, and can mate or cooperate with the mold 52 in a variety of ways. In addition, the cooperation between the positive and negative portions of the mold assemblies 51 and 53 is not limited to what is shown in FIG. 1.

As mentioned above, the first slurry 62 can include (i) a glass and/or glass ceramic powder; (ii) a liquid (e.g., water); (iii) a binder (e.g., an inorganic binder); and (iv) an activator (e.g., an acid or base). The formulation of the slurries of the present disclosure and exemplary methods of forming the slurries of the present disclosure are described in greater detail below. The slurries of the present disclosure can sometimes be referred to as "glass and/or glass ceramic" slurries.

In a second step 10B of the method, the first solid structure 54 can be pressed into the first slurry 62, forming the first layer 65 of the dental appliance. In such embodiments of the method 10 and system 50, the first solid structure 54 can function as a stamp that can be used to form a layer in the layered dental appliance but that will not necessarily remain as a component in the finished dental appliance.

However, it should be understood that in some embodiments, the desired dental appliance can include only one layer formed over a dental core or framework. In such embodiments, the first solid structure 54 can include the desired inner core of framework of the resulting dental appliance; the system 50 can include the first mold assembly 51 (i.e., and not the second mold assembly 53); and the method 10 can include steps 10A and 10B only. Such a system and method is exemplified in Example 2. Furthermore, in such embodiments, the construction shown in step 10B can be dried, the dental core 54 and the first layer 65 can be demolded or removed from the mold 52, and the two-layer dental appliance comprising the core 54 and the first layer 65 can optionally be further fired (e.g., under a vacuum) and/or machined.

As a result, in some embodiments, the first solid structure 54 can include or function as a stamp, and in some embodiments, the first solid structure 54 can include a dental core that forms a portion of the resulting dental appliance. Said another way, a "material" can be positioned in the first slurry 62. In some embodiments, the material includes a dental core, and the dental core forms a second layer of the dental appliance; and in some embodiments, the material includes a second slurry 72 (e.g., after the first solid structure 54 has been removed from the first slurry 62, as described in greater detail below). On the other hand, in some embodiments, the second slurry 72 can fill a cavity in the first slurry 62 to form a second layer (i.e., inner core) of the dental appliance, or the second slurry 72 can be pressed with the second solid structure 56 (as shown in FIG. 1 and described below) to form a second layer 75 of the dental appliance.

In some embodiments, any casting step of the present disclosure can be characterized by at least one of the following features:

duration: about 2 to about 5 seconds for 10 g of reaction mixture; and/or temperature: about 10 to about 40° C. or about 15 to about 30° C. or at ambient conditions (i.e., ambient temperature and pressure, e.g., 23° C., 1013 mbar).

In some embodiments, reducing the formation of air bubbles during the casting step can be avoided, for example, by applying reduced pressure.

As shown in FIG. 1, the entire construction comprising the first mold assembly 51 and the first slurry 62 pressed between the two (i.e., positive and negative) portions of the first mold assembly 51 (i.e., the mold 52 and the first solid structure 54) can be dried (e.g., at ambient conditions and/or in a drying oven at an elevated temperature) to harden the first slurry 62 and form the first layer 65 of the dental appliance.

Any drying step of the present disclosure can be characterized by at least one of the following features:

duration: up to about 24 h or up to about 8 h or up to about 1 h, temperature: from about 10 to about 120° C. or about 20 to about 100° C., and/or pressure: ambient pressure.

During the drying step, the network-formation of the binder can be finalized and low boiling components that may have been generated during the network forming process, if any, can evaporate from the cast mixture.

Drying can be performed at ambient conditions by simply letting the mold containing the mixture stand for a sufficient period of time. If a more rapid drying is desired, drying can be performed in a drying oven.

As shown in FIG. 1, in a third step 10C of the method 10, the first solid structure 54 can be removed from the mold 52 and the first slurry 62, leaving behind the first layer 65 that resembles a solid shell and comprises an outer shape or surface 66 of the dental appliance that corresponds to the inner (negative) surface 58 of the mold 52, and an inner (negative) shape 68 that corresponds to the outer (positive) surface 60 of the first solid structure 54. The inner (negative) shape 68 (or "cavity" or "second negative mold") of the first layer 65 includes a negative of the desired outer shape or surface of the next layer of the dental appliance.

However, in some embodiments, such a shell-like dental appliance is desired, and the resulting shell-like first layer 65 forms the desired dental appliance. In such embodiments, the method 10 comprises steps 10A-10C only, such that the method is complete following removal of the first solid structure 54 from the mold 52. In such embodiments, the first layer 65 can be dried, removed from the mold 52, and optionally further fired and/or machined.

A firing or sintering step of the present disclosure can be characterized by at least one of the following features:

duration: about 10 to about 60 min or about 20 to about 25 min, temperature: about 600 to about 900° C. or about 750 to about 850° C., pressure: about 10 to about 50 mbar or about 15 to about 35 mbar, and/or atmosphere: air.

Sintering can be conducted in a commercially available sinter furnace (e.g. Austromat 3001 from Dekema Comp.; Germany).

Sintering, if at all, can be conducted before the resulting dental appliance is machined or afterwards. In some embodiments when sintering is employed, the sintered material can have a density in a range of about 2 g/cm$^3$ to about 2.7 g/cm$^3$.

The sintered material can include a level of translucency. The translucency can be specified by the opacity of a material relative to daylight. In some embodiments, the opacity of the sintered material ranges from about 50% to about 60% (e.g., corresponding to natural dental enamel), in some embodiments from about 60% to about 80% (e.g., corresponding to natural dentine), and in some embodiments from about 80% to about 90% (e.g., corresponding to natural opaque dentine).

A machining step of the present disclosure can be characterized by at least one of the following features:
  machining can be accomplished under dry or wet conditions,
  milling parameter rotation: about 18,000 to about 32,000 rpm, and/or
  milling parameter motion: about 1,500 to about 2,500 mm per minute.

Other machining equipment as those mentioned in the above definition of machining can be used, if desired.

In a fourth step 10D of the method, the second mold assembly 53 is provided, and a second slurry 72 is positioned (e.g., cast) in the cavity 68 of the first layer 65. In addition, the second solid structure 56 can begin being moved toward or into the interior of the cavity 68 in the mold 52. The second solid structure 56 can include a positive shape or surface 70 corresponding to a third layer of the desired layered dental appliance.

While two mold assemblies 51 and 53 are shown in FIG. 1 by way of example only. It should be understood that in some embodiments, the system 50 can include only the first mold assembly 51. In such embodiments, the first solid structure 54 that is used in steps 10A-10C can be reused in steps 10D-10F of the method 10. In some embodiments, the first and second mold assemblies 51 and 53 are employed, but the two mold assemblies 51 and 53 are identical, such that the second solid structure 56 has the same shape as the first solid structure 54, but use of the second solid structure 56 eliminates the need for reusing the first solid structure 54. Still, in some embodiments, as shown in FIG. 1, the second solid structure 56 can have a different shape and/or a different (e.g., smaller) size than the first solid structure 54.

Some embodiments of the system 50 and method 10 do not include a second mold assembly 53 at all because the method 10 is complete following positioning the second slurry 72 in the cavity 68 (i.e., the method 10 comprises steps 10A-10D only). For example, in some embodiments, the second slurry 72 can be used to form an inner core of the resulting dental appliance, such that a second mold assembly 53 and a second solid structure 56 (or "stamp") is not necessary. The resulting two-layer dental appliance that comprises the first layer 65 and a core formed from the second slurry 72 can then be dried, removed from the mold 52, and optionally further fired and/or machined. Such a system and method is exemplified in Example 1.

Similar to the first slurry 62, the second slurry 72 can include (i) a glass and/or glass ceramic powder; (ii) a liquid (e.g., water); (iii) a binder (e.g., an inorganic binder); and (iv) an activator (e.g., an acid or base). The second slurry 72 can be the same formulation or a different formation as the first slurry 62.

In a fifth step 10E of the method 10 illustrated in FIG. 1, the second solid structure 56 can be pressed into the second slurry 72, forming the second layer 75 of the dental appliance. In such embodiments of the method 10 and system 50, the second solid structure 56 can also function as a stamp that can be used to form a layer in the layered dental appliance but that will not necessarily remain as a component in the finished dental appliance. However, it should be understood that, similar to the first solid structure 54 described above, in some embodiments, the second solid structure 56 can include a dental core or framework that is not removed and that forms the inner core of the resulting dental appliance. In such embodiments, the method 10 can include steps 10A-10E only. Furthermore, in such embodiments, the construction shown in step 10E can be dried, the dental core 56, the second layer 75, and the first layer 65 can be demolded or removed from the mold 52, and the three-layer dental appliance comprising the core 56, the second layer 75, and the first layer 65 can optionally be further fired (e.g., under a vacuum) and/or machined.

The second layer 75 is shown in FIG. 1 as being generally of the same thickness as the first layer 65. However, it should be noted that this need not be the case. In some embodiments, the first layer 65 can have the greatest thickness. For example, in some embodiments, there may be less volume or space available for forming the second layer 75 between the cavity 68 in the first layer 65 and the outer surface 70 of the second solid structure 56 than there was available for forming the first layer 65 between the inner surface 58 of the mold 52 and the first solid structure 54. Having less space available for forming the second layer 75 can result in the second layer 75 being thinner than the first layer 65. This can occur, for example, in embodiments in which the second solid structure 56 is generally a similar size as the first solid structure 54, or if the first solid structure 54 is reused to form the second layer 75. Alternatively, in some embodiments, the thickness of the layers can increase toward the center or inner core of the resulting appliance. For example, such embodiments can be achieved by employing different slurries that shrink differently during firing.

As shown in FIG. 1, in a sixth step 10F of the method 10, the second solid structure 56 can be removed from the mold 52 and the second slurry 72, leaving behind the second layer 75 and the first layer 65 that together form a two-layer solid shell and comprise an outer shape or surface 66 of the dental appliance that corresponds to the inner (negative) surface 58 of the mold 52, and an inner (negative) shape 78 that corresponds to the outer (positive) surface 70 of the second solid structure 56. The inner (negative) shape 78 or "cavity" of the second layer 75 includes a negative of the desired outer shape or surface of the next (third) layer of the dental appliance.

However, in some embodiments, such a shell-like dental appliance is desired, and the resulting two-layer shell forms the desired dental appliance. In such embodiments, the method 10 comprises steps 10A-10F only, such that the method is complete following removal of the second solid structure 56 from the mold 52. In such embodiments, the two-layer shell comprising the first layer 65 and the second layer 75 can be dried, removed from the mold 52, and optionally further fired and/or machined.

As shown in FIG. 1, in a seventh step 10G of the method 10, a third slurry 82 is positioned (e.g., cast) in the cavity 78 of the second layer 75. Similar to the first and second slurries, the third slurry 82 can include (i) a glass and/or glass ceramic powder; (ii) a liquid (e.g., water); (iii) a binder (e.g., an inorganic binder); and (iv) an activator (e.g., an acid or base). The third slurry 82 can be the same formulation or a different formation as one or both of the first slurry 62 and the second slurry 72.

By way of example only, in the system 50 and method 10 illustrated in FIG. 1, the third slurry 82 is shown as being used to form an inner core of the resulting dental appliance, such that a third mold assembly and a third solid structure is not necessary. However, in embodiments in which a dental appliance having more than three layers is desired, the process of positioning a slurry in the cavity of the previous layer and pressing the slurry with a solid structure (e.g., a stamp or positive portion of a mold) in order to form a next layer can be continued until desired. The construction shown in step 10G comprising the mold 52, the first layer 65, the second layer 75 and the third slurry 82 can be dried (e.g., at ambient conditions or in a drying oven at an elevated temperature) to harden the third slurry 82 and form the third layer 85 (i.e., core) of the dental appliance.

In an eighth step 10H of the method 10, a resulting three-layer dental appliance 90 comprising the first layer 65, the second layer 75 and the third layer 85 can then be removed from the mold 52, and optionally further fired (e.g., under a vacuum) and/or machined.

In some embodiments, the resulting dental appliance 90, or one or more layers of the dental appliance 90, may be substantially free of cells, voids or pores, or can include up to about 20 cells per $mm^2$. In some embodiments, the dental appliance 90, or one or more layers of the dental appliance 90 can include about 4 to about 10 cells per $mm^2$. In some embodiments, the cells can have a diameter of less than about 150 μm, in some embodiments less than about 100 μm, and in some embodiments less than about 50 μm.

In some embodiments, the volume of the cells in the dental appliance 90 (or one or more layers of the dental appliance 90), relative to the total volume of the dental appliance 90 (or relative to the total volume of the one or more layers of the dental appliance 90) can range from about 20% to about 40%, and in some embodiments can range from about 30% to about 38%. In some embodiments, these percentages refer to a pre-sintered state, not to a fully sintered glass or glass ceramic.

As can be understood by the above description of the method 10 and the system 50 of FIG. 1 and alternatives to the method 10 and the system 50, the present disclosure provides a multilayer dental appliance having two or more layers, wherein the innermost layer can include a solid structure (e.g., a dental core) and/or be formed of a slurry, such as a glass and/or glass ceramic slurry. Furthermore, the method 10 is shown by way of example only as including two "stamping" steps prior to forming the inner core of the dental appliance, in which a positive and negative mold are used together to form a layer of the dental appliance. However, it should be understood that as few as no removable solid structures (e.g., when the second (inner) layer of a two-layer dental appliance is provided by a dental core or framework) and as many as necessary can be employed to provide a dental appliance having a desired number of layers.

In addition, in the description above, the final dental appliance 90 and the method 10 used to make the dental appliance 90 are described as including and forming a first layer 65, a second layer 75 and a third layer 85. However, in some embodiments, the final dental appliance 90 can include many layers, and the method 10 for making the dental appliance 90 can include many repetitions of steps 10D-10F followed by steps 10G and 10H. In such embodiments, the method can be iterative, and the innermost layer can be referred to as "layer n," the next successive (outer) layer can be referred to as "layer n−1," the next successive (outer) layer can be referred to as "layer n−2," and so on, and the layers can be formed in the order of the outermost layer to the innermost layer, such that layer n, the innermost layer, is the last layer formed. In other words, each layer can be referred to as "layer n−x," where x runs from 0 to n−1 (from the innermost layer to the outermost layer). Said another way, the outermost layer can be referred to as "layer 1," the next successive (inner) layer can be referred to as "layer 2," the next successive (inner) layer can be referred to as "layer 3," and so on, and the final innermost layer can be referred to as "layer n," where the resulting layered dental appliance includes n layers.

In addition, by way of example only and for simplicity of illustration, the first and second solid structures 54 and 56 are shown as being pressed into the first and second slurries 62 and 72, respectively, until the solid structures 54 and 56 are flush with the top surfaces of the mold 52. However, the schematic shapes of the parts shown in FIG. 1 and the cooperation between such parts are shown in FIG. 1 by way of example only and for purposes of illustration, and are not intended to be limiting. In addition, in some embodiments, the solid structures 54 and 56 may not be pressed so far into the mold 52. In some embodiments, excess of one or more of the slurries 62 and/or 72 can be forced out of the mold 52 when the respective first and/or second solid structure 54 and/or 56 is moved into the mold 52. Such excess may need to be removed during downstream processing (e.g., machining).

The following description of the formulation of the slurry and exemplary methods of forming the slurry of the present disclosure can generally apply to each of the first slurry 62, the second slurry 72, and the third slurry 82 shown in FIG. 1, as well as to additional slurries that may be necessary in another embodiment of the method or system of the present disclosure. Other details and aspects regarding the mixture or slurry and inorganic gel casting of dental appliances can be found in EP Patent Application No. EP08165607.6, filed Oct. 1, 2008, entitled "Dental Appliance, Process for producing a dental appliance and Use thereof," the disclosure of which is incorporated herein by reference in its entirety.

Liquid

The nature and structure of the liquid to be used in a slurry of the present disclosure (e.g., the first slurry 62) is not particularly limited, unless the intended purpose cannot be achieved.

In some embodiments, the liquid can be characterized by at least one of the following features:
 boiling point: about 60 to about 120° C.,
 freezing point: about −120 to about 0° C., and/or
 density: about 0.7 to about 1.2 $g/cm^3$.

Specific examples of liquids include, but are not limited to, water, alcohols (including methanol, ethanol n- and iso-propanol), ketones (including acetone), and combinations thereof.

In some embodiments, the liquid can be present in an amount ranging from about 15 wt.-% to about 60 wt.-%, in some embodiments from about 20 wt.-% to about 40 wt.-%, and in some embodiments from about 25 wt.-% to about 35 wt.-%, with respect to the whole composition or mixture, respectively.

In some embodiments, the liquid can be present in an amount of at least about 15 wt.-%, in some embodiments at least about 20 wt.-%, and in some embodiments at least about 25 wt.-%, with respect to the whole composition or mixture, respectively.

In some embodiments, the liquid can be present in an amount of no greater than about 35 wt.-%, in some embodiments no greater than about 40 wt.-%, and in some embodiments no greater than about 60 wt.-%, with respect to the whole composition or mixture, respectively.

Inorganic Binder

The nature and structure of the inorganic binder to be used in a slurry is not particularly limited, either, unless the intended purpose cannot be achieved.

The inorganic binder can form an inorganic network upon initiating a curing or hardening reaction. The curing or hardening reaction can be initiated e.g. by adjusting the pH value, either by adding acidic or basic reagents including those described in more detail below.

The network formed by the inorganic binder can have a similar or essentially identical chemical nature or composition as the chemical nature or composition of the glass/glass ceramic powder/particles used.

In some embodiments, the inorganic binder can be a liquid at ambient conditions (e.g., 23° C.; 1013 mbar) or applied as an aqueous solution and can be characterized by at least one of the following features:

density: about 0.7 to about 1.5 g/cm$^3$ or about 0.9 to about 1.4 g/cm$^3$, molecular mass: about 100 to about 500 g/mol or about 150 to about 250 g/mol (for molecular precursors), containing Si and O, and/or producing low boiling by- or condensation products during hardening, if any (e.g. boiling point below about 120° C.).

Specific examples of inorganic binder precursors include, but are not limited to tetra alkyl (e.g. C1 to C4) orthosilicates (including tetramethyl orthosilicate (TMOS), tetraethyl orthosilicate (TEOS)), water glass and silica sol.

In some embodiments, the inorganic binder (e.g., silica) can be present in an amount ranging from about 0.1 wt.-% to about 40 wt.-%, in some embodiments from about 1.0 wt.-% to about 20 wt.-%, and in some embodiments from about 2.5 wt.-% to about 10 wt.-%, with respect to the solids content of the mixture, respectively.

In some embodiments, the inorganic binder can be present in an amount of at least about 0.1 wt.-%, in some embodiments at least about 1.0 wt.-%, and in some embodiments at least about 2.5 wt.-%, with respect to the solids content of the mixture, respectively.

In some embodiments, the inorganic binder can be present in an amount no greater than about 10 wt.-%, in some embodiments no greater than about 20 wt.-%, and in some embodiments no greater than about 40 wt.-%, with respect to the solids content of the mixture, respectively.

Glass and/or Glass Ceramic Powder

The nature and structure of the glass and/or glass ceramic powder to be used in a slurry is not particularly limited, either, unless the intended purpose cannot be achieved.

The glass and/or glass ceramic powder may consist essentially of, or consist only of a glass and/or glass ceramic material. The glass and/or glass ceramic material can be selected to be compatible for use in human bodies. Furthermore, the glass and/or glass ceramic material can be selected to provide good aesthetic appearance for the dental appliance.

In some embodiments, the glass and/or glass ceramic powder can be characterized by at least one of the following features:

mean particle size: range from about 5 μm to about 60 μm, or from about 10 to about 40 μm (measured with laser diffraction);

melting temperature: around or less than 1000° C. and/or density: about 2.0 to about 2.6 or about 2.2 to about 2.5 g/cm$^3$ (according to the technical data sheet provided by the manufacturer).

In some embodiments, a glass composition, which can be used, can include:

silica: about 60 to about 70 wt.-%,
alumina: about 9 to about 13 wt.-%,
potassium-oxide: about 5 to about 10 wt.-%,
sodium-oxide: about 9 to about 13 wt.-%,
lithium-oxide: about 0 to abut 1 wt.-%,
calcium oxide: about 2 to about 5 wt.-%,
barium-oxide: about 0 to about 2 wt.-% (optional),
zirconium oxide: about 0 to about 1 wt.-% (optional), and
cerium-oxide or cerium-fluoride: about 0 to about 1 wt.-% (optional).

Examples of glass and/or glass ceramic materials that can be used include those available under the designations: "VM 9" from Vita Zahnfabrik, Bad Säckingen, Germany, "Cerabien Zr" from Noritake Inc., Japan, "Vintage" from Shofu, Japan; "ZIROX" from Wieland GmbH & Co. KG, Pforzheim, Germany and LM-ZrO$_2$ from Chemichl, Liechtenstein.

In some embodiments, the glass and/or glass ceramic powder can be present in an amount of at least about 40 wt.-%, in some embodiments at least about 60 wt.-%, and in some embodiments at least about 65 wt.-%, with respect to the whole composition or mixture, respectively.

In some embodiments, the glass and/or glass ceramic powder can be present in an amount no greater than about 75 wt.-%, in some embodiments no greater than about 80 wt.-%, and in some embodiments no greater than about 85 wt.-%, with respect to the whole composition or mixture, respectively.

In some embodiments, the glass and/or glass ceramic powder can be present in an amount ranging from about 40 wt.-% to about 85 wt.-%, in some embodiments ranging from about 60 wt.-% to about 80 wt.-%, and in some embodiments ranging from about 65 wt.-% to about 75 wt.-%, with respect to the whole composition or mixture, respectively.

The distribution of the particle size may be for example:

10% of the particles smaller than about 5 μm or smaller than about 2 μm;

50% of the particles smaller than about 25 μm or smaller than about 10 μm; and

90% of the particles smaller than about 70 μm or smaller than about 40 μm.

Additives

A mixture or slurry of the present disclosure can also comprise further components or additives, such as colorant(s) and/or pigments (e.g. traces of fluorescent, organic pigments e.g. for easier identification of the blocks ("labeling"), which can be burnt out during firing; and/or inorganic pigments that remain in the appliance for coloration of the sintered material). Such additives or components can also be present or included in the glass and/or glass ceramic powder or particles. Suitable colorants can include one or more of the following elements or ions thereof: Fe, Mn, V, Cr, Zn, Sn and Co.

Further additives, which can be added, can include retarders, (such as 1,2-diphenylethylene), plasticizers (including polyethylene glycol derivatives, polypropylene glycols, low-molecular-weight polyesters, dibutyl, dioctyl, dinonyl and diphenyl phthalate, di(isononyl adipate), tricresyl phosphate, paraffin oils, glycerol triacetate, bisphenol A diacetate, ethoxylated bisphenol A diacetate, silicone oils, or a combination thereof), fluoride releasing materials, or a combination thereof.

Some embodiments include no additives, however, if they are present, they can be present in an amount of at least about 0.01 wt.-%, in some embodiments at least about 0.1 wt.-%, and in some embodiments at least about 1 wt.-%, with respect to the whole composition or mixture, respectively.

In some embodiments, additives can be present in an amount no greater than about 20 wt.-%, in some embodiments no greater than about 10 wt.-%, and in some embodiments no greater than about 5 wt.-%, with respect to the whole composition or mixture, respectively.

In some embodiments, additives can be included in amounts ranging from about 0.01 to about 20 wt.-%, in some embodiments ranging from about 0.1 to about 10 wt.-%, and in some embodiments ranging from about 1 to about 5 wt.-%.

As long as the additive does not influence the sol-gel reaction, it can be employed in any desired amount with respect to the whole composition or mixture.

In some embodiments, a slurry or mixture to be used in the casting process of the present disclosure can include the individual components in the following amounts:

- liquid: from about 15 wt.-% to about 60 wt.-%, or from about 20 wt.-% to about 40 wt.-%, or from about 25 wt.-% to about 35 wt.-%, with respect to the whole weight of the mixture;
- inorganic binder: from about 0.1 wt.-% to about 40 wt.-%, or from about 1 wt.-% to about 20 wt.-%, or from about 2.5 wt.-% to about 10 wt.-%, with respect to the solids content of the mixture;
- glass and/or glass ceramic powder: from about 40 wt.-% to about 85 wt.-%, or from about 60 wt.-% to about 80 wt.-%, or from about 65 wt.-% to about 75 wt.-%, with respect to the whole weight of the mixture; and
- additives (including colorant(s)): from about 0.01 to about 20 wt.-%, or from about 0.1 to about 10 wt.-%, or from about 1 to about 5 wt.-%, with respect to the whole weight of the mixture.

In some embodiments, the ratio (with respect to weight) of liquid to inorganic binder can be a range of about 10:1 to about 1:1, or from about 7:1 to about 3:1. If the ratio is outside this range, the obtained dental appliance may not include the desired properties.

In some embodiments, the ratio (with respect to weight) of inorganic binder to glass and/or glass ceramic powder can be in a range of about 1:100 to about 1:5, or from about 1:40 to about 1:10. If the ratio is outside this range, the obtained dental appliance may not include the desired properties.

Forming the Slurry

In some embodiments, the slurry or mixture can be obtained by the following exemplary process:

i) providing a liquid,
ii) adjusting the liquid to a pH value suitable to start the condensation reaction, depending on the binder precursor used (e.g. 10 to about 12 for TMOS or about 2 to about 4 for water glass),
iii) adding the glass and/or glass ceramic powder, and
iv) adding the inorganic binder,
wherein steps iii) and iv) can also be carried out in reverse order.

The pH value can be adjusted by using conventional basic reagents like NaOH, KOH or $NH_3$ containing solutions or acidic reagents like HCl or $HNO_3$ containing solutions, wherein the pH value can be determined during the adjustment step. The pH value can be determined by e.g. pH sensitive paper or electronic equipment (e.g. pH electrode). If strong acids or bases are employed, determination of the pH value can also be obtained via calculation from the amount of acid used.

The inorganic binder can be added rapidly while the solution is stirred. The addition of the inorganic binder can mark the starting point of a sol-gel reaction caused by the reaction of the inorganic binder molecules. In some embodiments, a two-slurry system can be used. If a two-slurry system ("I" and "II") is used, mixing of the two slurries marks the starting point of the sol-gel reaction.

During the sol-gel reaction, an inorganic network can be formed.

In some embodiments, providing a slurry or mixture can be characterized by at least one of the following features:

- time needed for gelation (i.e. time from adding the inorganic binder until solidification of the mixture to the point that it cannot be deformed or removed from the mold by tilting the mold): 30 seconds to 5 minutes; and/or
- time needed for settling (i.e., time from stopping the mixture being stirred until the mixture becomes inhomogeneous because of settling of the glass and/or glass ceramic particles): 7 minutes to more than one week (values were obtained either without inorganic binder present or with binder present but at a pH value that inhibits gelation).

The mixtures or slurries to be used in the process of the present disclosure typically do not contain polymerizable organic binder components like (meth)acrylate or epoxy groups containing components.

That is, in some embodiments, the mixture is essentially free of polymerizable organic binder components. An organic binder within the meaning of the invention is a binder, which consists of organic compounds that are added to strengthen the appliance or workpiece and cannot be thermally removed from the workpiece below a temperature of 200° C. Organic binders can produce gases like carbon oxide(s) or nitrogen oxide(s) when heated above the combustion temperature. These exhaust gases may have to be removed by expensive air treatment or chimneys.

In some embodiments, the addition or presence of an initiator (e.g. photo or redox initiator) for starting the hardening process of the inorganic binder is typically not needed. The hardening process can be initiated by adjusting the pH value or simply by employing a diluted acidic/basic solution.

The production process of the present disclosure typically also does not include a pressing step (e.g. isostatic or uniaxial) or a pre-sintering step.

The following embodiments are intended to be illustrative of the present disclosure and not limiting.

Embodiments

Embodiment 1 is a method for making a layered dental appliance, the method comprising: providing a mold comprising a negative of an outer shape of a layered dental appliance; positioning a slurry in the mold, forming a first layer of the layered dental appliance; providing a solid structure comprising a positive shape of a second layer of the layered dental appliance; pressing the solid structure into the slurry in the mold.

Embodiment 2 is the method of embodiment 1, wherein the solid structure includes at least one of a dental core and a stamp.

Embodiment 3 is the method of embodiment 1, wherein pressing the solid structure into the slurry includes pressing a dental core into the slurry, such that the dental core forms at least a portion of the second layer.

Embodiment 4 is the method of embodiment 1, further comprising removing the solid structure from the slurry.

Embodiment 5 is the method of embodiment 1 or 4, wherein the solid structure includes a stamp, and further comprising removing the stamp from the slurry to form a cavity comprising a negative of the second layer in the slurry.

Embodiment 6 is the method of embodiment 5, further comprising using the cavity as a mold for a second layer of the dental appliance.

Embodiment 7 is the method of embodiment 5 or 6, wherein the slurry is a first slurry, and further comprising positioning a second slurry in the cavity to form a second layer of the layered dental appliance.

Embodiment 8 is the method of embodiment 7, wherein the first slurry has a different composition than the second slurry.

Embodiment 9 is the method of embodiment 7 or 8, further comprising pressing a dental core into the second slurry, such that the core forms at least a portion of a third layer of the layered dental appliance.

Embodiment 10 is the method of embodiment 7 or 8, further comprising: providing a second solid structure comprising a positive shape of a third layer of the layered dental appliance; and pressing the second solid structure into the second slurry.

Embodiment 11 is the method of embodiment 10, wherein pressing the second solid structure into the second slurry includes pressing a dental core into the second slurry, such that the dental core forms at least a portion of the third layer.

Embodiment 12 is the method of embodiment 10, wherein the second solid structure includes a second stamp, and further comprising removing the second stamp from the second slurry to form a second cavity comprising a negative of a third layer of the dental appliance.

Embodiment 13 is the method of embodiment 12, further comprising positioning a third slurry in the second cavity to form a third layer of the dental appliance.

Embodiment 14 is the method of embodiment 13, wherein the third slurry has the same composition as at least one of the first slurry and the second slurry.

Embodiment 15 is a method for making a layered dental appliance, the method comprising: providing a mold comprising a negative of a first layer of a layered dental appliance; providing a stamp comprising a positive shape of a second layer of the layered dental appliance; positioning a first slurry in the mold; pressing the stamp into the first slurry in the mold to form a cavity comprising a negative of the second layer in the first slurry; removing the stamp from the first slurry; and positioning a material in the cavity to form another layer of the layered dental appliance, wherein the material comprises at least one of a dental core and a second slurry.

Embodiment 16 is the method of embodiment 15, wherein positioning a material in the cavity includes positioning a second slurry in the cavity.

Embodiment 17 is the method of embodiment 15 or 16, further comprising: providing a second stamp comprising a positive shape of a third layer of the layered dental appliance; pressing the second stamp into the material to form a second cavity comprising a negative of the third layer in the material; and positioning a material in the second cavity to form the third layer of the layered dental appliance, wherein the material comprises at least one of a dental core and a third slurry.

Embodiment 18 is the method of embodiment 17, wherein the third layer forms the inner core of the layered dental appliance.

Embodiment 19 is the method of embodiment 17 or 18, wherein positioning a material in the second cavity includes positioning a third slurry in the second cavity.

Embodiment 20 is the method of embodiment 19, wherein the third slurry is the same composition as at least one of the first slurry and the second slurry.

Embodiment 21 is the method of embodiment 15 or 16, wherein the material includes a second slurry, and further comprising pressing a dental core into the second slurry, such that the dental core forms at least a portion of a third layer of the layered dental appliance.

Embodiment 22 is the method of embodiment 15, wherein the material includes a dental core, and further comprising: prior to positioning the dental core in the cavity, positioning a second slurry in the cavity, and wherein positioning a material in the cavity includes pressing the dental core into the second slurry positioned in the cavity of the first slurry.

Embodiment 23 is the method of embodiment 15, wherein the material includes a dental core, and further comprising: preparing a wax-up of the dental core, such that the wax-up comprises a positive shape of the desired dental appliance; preparing the mold with the wax-up; removing the wax-up from the mold; removing the wax from the dental core; and using the dental core as the material for the second layer.

Embodiment 24 is the method of any of embodiments 1-23, wherein the first layer forms the outermost layer of the layered dental appliance.

Embodiment 25 is a method for making a layered dental appliance having n layers, the method comprising: providing a mold comprising a negative of a layer n–1 of a layered dental appliance; positioning a slurry in the mold to form layer n–1 of the layered dental appliance; and pressing a dental core in the slurry, such that the dental core forms at least a portion of a layer n of the layered dental appliance.

Embodiment 26 is the method of embodiment 25, wherein the slurry is a second slurry and the mold is a second mold, and further comprising: providing a first mold comprising a negative of a layer n–2 of the layered dental appliance; providing a stamp comprising a positive shape of layer n–1 of the layered dental appliance; positioning a first slurry in the mold to form layer n–2 of the layered dental appliance; and pressing the stamp into the first slurry in the first mold to provide the second mold comprising a negative of the layer n–1 in the first slurry.

Embodiment 27 is the method of embodiment 26, further comprising removing the stamp from the first slurry.

Embodiment 28 is the method of any of embodiments 1-14 and 24-27, further comprising activating the slurry prior to positioning the slurry in the mold.

Embodiment 29 is the method of any of embodiments 1-14 and 24-28, further comprising initiating a sol-gel reaction in the slurry prior to positioning the slurry in the mold.

Embodiment 30 is the method of any of embodiments 1-14 and 24-29, wherein the slurry comprises at least one of a glass slurry, a glass ceramic slurry, and a combination thereof.

Embodiment 31 is the method of any of embodiments 1-14 and 24-30, further comprising drying the slurry after positioning the slurry in the mold.

Embodiment 32 is the method of any of embodiments 1-31, wherein at least a portion of the mold is formed of at least one of silicone, polyethylene (PE), polypropylene (PP), polycarbonate, polyurethane, polystyrene, polyoxymethylene, a metal, and a combination thereof.

Embodiment 33 is the method of any of embodiments 1-32, wherein providing a mold comprising a negative includes providing a mold comprising an enlarged negative.

Embodiment 34 is the method of any of embodiments 1-33, wherein providing the mold includes preparing a mold based on a digital workflow.

Embodiment 35 is the method of any of embodiments 1-34, further comprising: removing the layered dental appliance from the mold; and firing the layered dental appliance.

Embodiment 36 is the method of embodiment 35, wherein firing the first article includes firing the first article at a temperature of at least 500° C.

Embodiment 37 is the method of any of embodiments 1-36, further comprising machining the layered dental appliance.

Embodiment 38 is the method of any of embodiments 1-37, further comprising: removing the layered dental appliance from the mold, the layered dental appliance comprising a near-net shape; and machining the layered dental appliance to a net shape.

Embodiment 39 is a system for making a layered dental appliance, the system comprising: a first portion comprising a negative of a first layer of a layered dental appliance; a second portion comprising a positive shape of a second layer of the layered dental appliance; and a first slurry configured to be positioned between the first portion and the second portion, such that the first slurry forms the first layer of the layered dental appliance.

Embodiment 40 is the system of embodiment 39, wherein the second portion comprises a dental core, such that the dental core forms the second layer of the layered dental appliance.

Embodiment 41 is the system of embodiment 39, further comprising a third portion comprising a positive shape of a third layer of the layered dental appliance.

Embodiment 42 is the system of embodiment 41, wherein the third portion comprises a dental core, such that the dental core forms at least a portion of the third layer of the layered dental appliance.

Embodiment 43 is a system for making a layered dental appliance, the system comprising: a first portion comprising a negative of a first layer of a layered dental appliance; a second portion comprising a positive shape of a second layer of the layered dental appliance; and a third portion comprising a positive shape of a third layer of the layered dental appliance.

Embodiment 44 is the system of embodiment 43, wherein the second layer is positioned inwardly with respect to the first layer, and the third layer is positioned inwardly with respect to the second layer of the layered dental appliance.

Embodiment 45 is the system of embodiment 43 or 44, wherein the second portion includes a first stamp, and wherein the third portion includes a second stamp.

Embodiment 46 is the system of any of embodiments 43-45, wherein the second portion and the third portion have the same shape.

Embodiment 47 is the system of any of embodiments 43-46, wherein the third portion is smaller than the second portion.

Embodiment 48 is the system of any of embodiments 43-47, wherein the third portion has a different shape and size than the second portion.

Embodiment 49 is the system of embodiments 43 or 44, wherein the second portion includes a stamp, and wherein the third portion includes a dental core that forms at least a portion of the third layer of the layered dental appliance.

Embodiment 50 is the method of any of embodiments 1-24 and 28-38 or the system of any of embodiments 39-49, wherein the second layer is positioned inwardly with respect to the first layer of the layered dental appliance.

Embodiment 51 is the method of any of embodiments 1-38 and 50 or the system of any of embodiments 39-42 and 50, wherein the slurry includes at least one of a glass slurry and a glass ceramic slurry.

Embodiment 52 is the method of any of embodiments 2, 3, 9, 11, 15-38 and 50-51 or the system of any of embodiments 40, 42, and 49-51, wherein the dental core includes at least one of a ceramic, a metal, a metal alloy, a precious metal, a precious metal alloy, and a combination thereof.

The following working examples are intended to be illustrative of the present disclosure and not limiting.

EXAMPLES

Example 1

Formation of a Two-Layer Dental Restoration

A plastic box having a precisely fitting lid was used to house and align the negative and positive portions of a mold, the negative portion of which was formed of silicone, and the positive portion of which was formed of polyoxymethylene (available under the trade designation DELRIN from DuPont Corp., Wilmington, Del.). The positive portion (stamp) was formed into the shape of a typical incisor by milling a block of polyoxymethylene using a LAVA™ Form M148 Mill (available from 3M ESPE AG, Seefeld, Germany). The base of this stamp was adhered to the inside of the box lid using Scotch-Weld adhesive (available from 3M Company, St. Paul, Minn.). The bottom of the box was filled with polydimethyl methylphenyl siloxane (Heraform, type A+B, Heraeus Kulzer, Germany) and the lid was placed onto the box, thus forcing the stamp into the silicone. The silicone was allowed to cure and the lid was removed, leaving a negative shape of the stamp, which corresponds to the outer shape of the desired dental restoration.

Without removing the stamp from the lid, a thin layer (about 1 mm) from the stamp's surface was removed using a dental grinding tool, thus forming a smaller stamp having the positive shape of a desired inner layer of the dental restoration.

A first slurry was prepared by mixing 9.8 ml of 1 mM sodium hydroxide (Fluka/Sigma-Aldrich, Germany) solution in deionized water and 25.0 g of white glass powder (LAVA™ Ceram E1, 3M ESPE). To the mixture, 2.0 ml of 98% tetramethyl orthosilicate (Fluka/Sigma-Aldrich) was added and stirred, thus initiating the hardening reaction. Forty seconds later, the slurry was poured into the negative portion of the mold and the lid of the box was attached, thus forcing the stamp having the shape of the inner layer into the slurry. After gelling for 20 min. at room temperature, the mold was placed into a drying oven (Memmert, Germany) at 50° C. for 60 min. After removal from the oven and cooling, the lid was removed from the box, leaving a solidified shell having the outer shape/surface of the desired dental restoration and an inner shape/surface of the inner layer.

A second slurry was prepared by mixing 9.8 ml of 1 mM sodium hydroxide solution in deionized water and 25.0 g of brown glass powder Dentin A4 (Chemichl, Liechtenstein) (brown glass was used for the purpose of visualization). To the mixture, 2.0 ml of 98% tetramethyl orthosilicate (Fluka/Sigma-Aldrich) was added and stirred. Thirty seconds after the addition, the slurry was poured into the mold, the solidified shell still in place. Since this was the final layer, no stamp was forced into the slurry, which was allowed to gel at room temperature for 15 min. and dried at 50° C. for 180 min.

The resulting solidified two-layer dental restoration was removed from the mold and fired under vacuum in an Austromat 3001 furnace (Dekema, Germany) at 780° C. for 25 min. to form a tooth (incisor)-shaped block.

The resulting incisor-shaped block was white at the labial surface and edges. The inner brown core was able to be seen through thin portions of the white outer layer and at the palatinal surface of the tooth.

Example 2

Formation of a Two-Layer Restoration

A three-unit Zirconia bridge core was formed using a LAVA™ digital system (3M ESPE). This bridge became the inner core of the finished restoration. Molten wax was layered onto the core, cooled, then shaped to form a "wax-up" having the final outer shape of a three-unit bridge. The thickness of the wax layer on the core was approximately 1 mm.

A mold was formed in two halves, a base half being a negative of the bridge base (i.e. the portion mating with the prepared tooth stumps) and an occlusal half being a negative of the bridge occlusal surfaces.

Beginning with the base half mold, the base of the wax-up was embedded into silicone impression material (VPS Impression Material, 3M ESPE), leaving the occlusal half uncovered by silicone. The silicone was allowed to cure and was further partially embedded in a block of wet plaster (Fixare Presto Plus, Picodent, Germany) which, when hardened, became a support structure for the cured silicone mold.

To form the occlusal half of the mold, the base half (silicone, and plaster) was coated with Vaseline to provide eventual release, then a layer of silicone was applied to the exposed occlusal half of the bridge core wax-up and cured. Again, a plaster support layer was applied to the cured silicone.

Once the plaster hardened, the two halves of the mold were separated and the wax-up was removed from the mold. The wax was scraped away from the bridge core, which was further cleaned by heating at 500° C. for 1 min. in a furnace (HTC 03/169, Nabertherm, Germany). The mold halves were also cleaned of Vaseline.

A slurry was prepared by mixing 8 g of glass powder (GM/LM-Zr, Chemichl, Liechtenstein), 2.5 ml of deionized water, and 1 g of pure sodium silicate (Sigma-Aldrich, Germany). The wax-free zirconia core was again pressed into the base half of the mold and slurry was placed into the occlusal half of the mold. One drop of 1 M hydrochloric acid was added to the liquid slurry in the mold, thus initiating the hardening process. The base half of the mold having the core was pressed into the slurry and the halves were clamped together. The mold was heated in a 50° C. oven for 12 hours, the mold was cooled and separated, and the layered bridge was removed.

The restoration was completed by firing at 790° C. for 15 min. in a furnace. The completed bridge restoration had a zirconia core and base shaped to fit onto prepared tooth stumps, and an outer glass veneer formed into the desired tooth shapes.

The embodiments described above and illustrated in the FIGURE are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure. Various features and aspects of the present disclosure are set forth in the following claims.

What is claimed is:

1. A method for making a layered dental appliance, the method comprising:
   providing a mold comprising a negative of an outer shape of the layered dental appliance;
   positioning a slurry in the mold, forming a first layer of the layered dental appliance, the slurry comprising:
   (i) at least one of a glass powder and a glass ceramic powder, present in an amount of about 60 wt.-% to about 85 wt.-%,
   (ii) a liquid, and
   (iii) an inorganic binder precursor;
   providing a solid structure comprising a positive shape of a second layer of the layered dental appliance, wherein the solid structure includes a stamp;
   pressing the solid structure into the slurry in the mold; and
   removing the solid structure from the slurry to form a cavity comprising a negative of the second layer in the slurry.

2. The method of claim 1, further comprising using the cavity as a mold for the second layer of the dental appliance.

3. The method of claim 1, wherein the slurry is a first slurry, and further comprising positioning a second slurry in the cavity to form the second layer of the layered dental appliance.

4. The method of claim 3, further comprising pressing a dental core into the second slurry, such that the core forms at least a portion of a third layer of the layered dental appliance.

5. The method of claim 3, further comprising:
   providing a second solid structure comprising a positive shape of a third layer of the layered dental appliance; and
   pressing the second solid structure into the second slurry.

6. The method of claim 5, wherein the second solid structure includes a second stamp, and further comprising removing the second solid structure from the second slurry to form a second cavity comprising a negative of the third layer in the second slurry.

7. The method of claim 6, further comprising positioning a third slurry in the second cavity to form a third layer of the dental appliance.

8. The method of claim 6, further comprising using the second cavity as a mold for the third layer of the dental appliance.

9. The method of claim 1, wherein the first layer forms the outermost layer of the layered dental appliance.

10. The method of claim 1, further comprising activating the slurry prior to positioning the slurry in the mold.

11. The method of claim 1, further comprising initiating a sol-gel reaction in the slurry prior to positioning the slurry in the mold.

12. The method of claim 1, further comprising:
   removing the layered dental appliance from the mold; and
   firing the layered dental appliance,
   wherein firing the first article includes firing the first article at a temperature of at least 500 ° C.

13. The method according to claim 1, the inorganic binder precursor being selected from orthosilicates, silica sol, water glass, mixtures and combinations thereof.

14. The method according to claim 1, wherein the mixture is essentially free of polymerizable organic binder components.

15. The method according to claim 1, further comprising:
   removing the layered dental appliance from the mold; and
   machining the dental appliance.

16. The method according to claim 15, wherein machining the dental appliance includes machining the dental appliance prior to sintering the dental appliance.

* * * * *

UNITED STATES PATENT AND TRADEMARK OFFICE
CERTIFICATE OF CORRECTION

| | | |
|---|---|---|
| PATENT NO. | : 9,039,947 B2 | Page 1 of 1 |
| APPLICATION NO. | : 13/497359 | |
| DATED | : May 26, 2015 | |
| INVENTOR(S) | : Michael Jahns | |

It is certified that error appears in the above-identified patent and that said Letters Patent is hereby corrected as shown below:

SPECIFICATION

Column 5
Line 19, Delete "thereof" and insert -- thereof; --, therefor.

Column 17
Line 64, Delete "abut" and insert -- about --, therefor.

Signed and Sealed this
Fifth Day of January, 2016

Michelle K. Lee
*Director of the United States Patent and Trademark Office*